United States Patent [19]

Plueddemann

[11] Patent Number: 4,503,242

[45] Date of Patent: Mar. 5, 1985

[54] STABILIZATION OF AQUEOUS SILICATES USING ALKALI SILICONATES OF SILYLORGANOSULFONATES

[75] Inventor: Edwin P. Plueddemann, Midland, Mich.

[73] Assignee: Dow Corning Corporation, Midland, Mich.

[21] Appl. No.: 467,695

[22] Filed: Feb. 18, 1983

[51] Int. Cl.³ .................... C07F 7/08; C07F 7/10
[52] U.S. Cl. .................... 556/401; 556/413; 556/419; 556/424; 556/425; 252/75; 252/78.3; 252/389 R
[58] Field of Search ............... 556/413, 401, 419, 424; 252/389 R, 78.3, 75

[56] References Cited

U.S. PATENT DOCUMENTS

| | | | |
|---|---|---|---|
| 2,968,643 | 1/1961 | Bailey | 260/46.5 |
| 3,198,820 | 8/1965 | Pines et al. | 260/448.2 |
| 3,234,144 | 2/1966 | Morehouse | 556/413 X |
| 3,312,622 | 4/1967 | Pines et al. | 252/75 |
| 3,328,449 | 6/1967 | Haluska | 260/448.2 |
| 3,337,496 | 8/1967 | Pines et al. | 260/46.5 |
| 3,341,469 | 9/1967 | Pines et al. | 252/389 |
| 3,819,675 | 6/1974 | Plueddemann | 556/413 |
| 3,948,964 | 4/1976 | Barfurth et al. | 260/448.8 |
| 4,203,913 | 5/1980 | Burkhardt et al. | 556/401 |
| 4,333,843 | 6/1982 | Wing et al. | 252/75 |
| 4,352,742 | 10/1982 | Davis et al. | 252/75 |
| 4,354,002 | 10/1982 | Davis et al. | 524/588 |
| 4,362,644 | 12/1982 | Davis et al. | 252/389 |
| 4,370,255 | 1/1983 | Plueddemann | 252/389 |

Primary Examiner—Paul F. Shaver
Attorney, Agent, or Firm—James E. Bittell

[57] ABSTRACT

Alkali siliconates of silylorganosulfonates are capable of stabilizing solutions of water soluble silicates and enhancing their usefulness as corrosion inhibitors for metals that come in contact with aqueous, alcoholic or aqueous-alcoholic solutions. The disclosed alkali siliconates of silylorganosulfonates are also useful stabilizers for aqueous silicates in such applications as treating boiler water, geothermal water and cooling coil water. Methods of using the alkali siliconates of silylorganosulfonates to provide corrosion inhibiting antifreeze and coolant solutions are disclosed.

70 Claims, No Drawings

STABILIZATION OF AQUEOUS SILICATES USING ALKALI SILICONATES OF SILYLORGANOSULFONATES

BACKGROUND OF THE INVENTION

This invention relates to novel silylorganosulfonates and their use in the stabilization of aqueous silicates.

Aqueous silicates as a class of compounds can take a role as useful materials, or they can in some circumstances be considered to be nuisances. For example, silicates are purposely added to antifreeze compositions as corrosion inhibitors, while certain silicates occurring in other kinds of heat transfer systems cause many problems by precipitating from solution and depositing on the interior surfaces of the heat transfer system which causes a reduction in efficiency.

For a long time, it has been a goal of the automotive antifreeze producers to find an efficient, low-cost method of maintaining the silicate corrosion inhibitors in solution; likewise, it has been a goal of engineers to find some method by which the naturally occurring soluble silicates could be maintained in solution so as to prevent their buildup on the interior surfaces of the heat transfer systems, and thus enhance the efficiency of the heat transfer systems. There have been many efforts therefore to stabilize silicates so that they could be more persistent in their corrosion inhibiting properties.

Arthur N. Pines et al. in U.S. Pat. Nos. 3,312,622 and 3,198,820 describe combinations of silicone-silicate polymers as corrosion inhibitors. Although the patent does not specifically describe the stabilization of silicates, it is very obvious from the specification that the so-called "novel organosilicon polymer" does, in fact, contribute to the persistency of the corrosion inhibition of the silicone-silicate polymers of that invention. The novelty, as pointed out therein, is the use of silyl carboxylates in conjunction with the silicates. Such materials are discussed as enhancing the corrosion inhibition of common antifreeze compositions and overcome disadvantages of other prior art corrosion inhibitors such as handling and dispensing of the antifreezes; selective corrosion inhibition of certain metals, poor shelf life, tendency to attack rubber hoses, excessive foaming in use and the causing of alcohols to decompose.

In later issued patents, U.S. Pat. Nos. 3,341,469 and 3,337,496, Pines et al. describe another system that was found useful for inhibiting corrosion in aqueous alcohol compositions. It consisted of a mixture of an alkyl silsesquioxane, a siloxane modified with a cyanoalkyl or carbinol group, and a silicate. These materials are stated as being "remarkably soluble in aqueous liquids". Further, the compositions are alleged to overcome many of the above-mentioned disadvantages.

U.S. Pat. No. 3,948,964, issued Apr. 6, 1976, describes the stabilization of partially hydrolyzed silicic acid esters using stabilizers selected from organic compounds such as cyclic ethers, ether alcohols, carboxylic acid esters and ketones. Such stabilized materials are described as binders for zinc dust pigments and the like.

U.S. Pat. No. 4,333,843, issued June 8, 1982, and U.S. Pat. No. 4,370,255, issued Jan. 25, 1983, describe gellation resistant aqueous glycol compositions useful as antifreezes, which glycol compositions contain an organophosphorus-silicon compound to stabilize the silicates in the composition and act as a corrosion inhibitor for metals with which the compositions come in contact.

In a recent publication, E. Plueddemann, *Silane Coupling Agents*, 62–72 (1982), it was reported that sodium siliconate silylpropylsulfonate, $NaO_{3/2}SiCH_2CH_2CH_2SO_3Na$, was marginally active in stabilizing silicate solutions against gelling. The silicate stabilizing effect of sulfonate functional silicate, however, was described as poor in comparison with phosphonate functional siliconate. U.S. Pat. No. 4,354,002, issued Oct. 12, 1982, claims copolymers of silicate and aliphatic silicone sulfonates as corrosion inhibitors of improved stability. Useful silicone compounds described in this patent have a sulfonate group attached to silicon by an aliphatic hydrocarbon unit and are represented by the siliconate silylpropylsulfonate also reported in the above publication by E. Plueddemann. U.S. Pat. No. 4,352,742, issued Oct. 5, 1982, claims corrosion inhibitors that are copolymers of silicate and a somewhat different sulfonate functional silicon compound. In the copolymers of this patent, the sulfonate group is attached to silicon by an aliphatic hydroxy-substituted group in which the hydroxy substituent is bonded to a carbon atom adjacent to the carbon atom to which the sulfonate group is attached. U.S. Pat. No. 4,362,644, issued Dec. 7, 1982, claims corrosion inhibitors that are copolymers of silicate and sulfonate functional silicones. In the copolymers of this patent, the sulfonate group is bonded to an aryl group and the aryl group is attached to silicon via a 2 to 4 carbon alkylene bridge.

Bailey discloses in U.S. Pat. No. 2,968,643 sulfoaralkylsilicon compounds for use in the form of their sulfonate salts as anti-fog agents for glass surfaces. Beta-(sulfophenyl)ethyl polysiloxane, $HO_3SC_6H_4CH_2CH_2SiO_{3/2}$, is representative of the compounds disclosed by Bailey. Haluska discloses in U.S. Pat. No. 3,328,449 sulfopropylated organofunctional silanes and siloxanes that are useful as detergents, ion exchange resins, wetting agents, antistat agents for synthetic fibers, and polymerization catalyst for siloxanes. The silane, $(CH_3O)_3Si(CH_2)_3NH(CH_2)_2NH(CH_2)_3SO_3H$, is representative of the compounds disclosed by Haluska.

None of the above references, however, describe the siliconate compositions of the instant invention. The advantages of the prior art methods can be obtained with the instant invention and additional advantages over the prior art are obtained by this invention. Most notable are the advantages of low cost, enhanced effectiveness in stabilization of silicates and the persistency of corrosion inhibition.

THE INVENTION

This invention consists of the use of alkali siliconate silylorganosulfonates in many varied applications. Further disclosed herein are unique compositions which are combinations of the aforementioned sulfonates and soluble silicates and their uses in many varied applications.

Thus, one aspect of this invention is a composition of matter which comprises an aqueous solution of an alkali siliconate silylorganosulfonate wherein the siliconate has the general formula

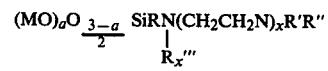

wherein R is a divalent alkylene radical of 3 or 4 carbon atoms; R' is a monovalent radical selected from a group consisting essentially of hydrogen and —(CH$_2$)$_n$SO$_3$M; R" is a monovalent radical selected from a group consisting essentially of —(CH$_2$)$_n$SO$_3$M and

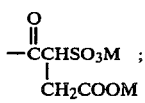

R''' is R' or R", M in all formulas is an alkali cation; n in all formulas has a value of 1, 2 or 3; x has a value of 0 or 1; and a has an average value of 0 to 3.

A further aspect of this invention is a composition of matter which comprises an alcoholic solution of an alkali siliconate silylorganosulfonate wherein the siliconate has the general formula

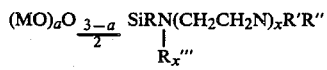

wherein R is a divalent alkylene radical of 3 or 4 carbon atoms; R' is a monovalent radical selected from a group consisting essentially of hydrogen and —(CH$_2$)$_n$SO$_3$M; R" is a monovalent radical selected from a group consisting essentially of —(CH$_2$)$_n$SO$_3$M and

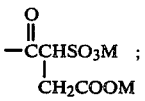

R''' is R' or R", M in all formulas is an alkali cation; n in all formulas has a value of 1, 2 or 3; x has a value of 0 or 1; and a has an average value of 0 to 3.

Further the invention disclosed herein consists of a composition of matter which is a combination of novel silylorganosulfonates and soluble silicates. This invention, therefore, consists of a composition of matter which is a mixture comprised of (A) water; (B) an alkali siliconate silylorganosulfonate which has the general formula

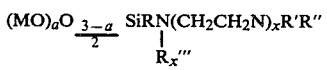

wherein R is a divalent alkylene radical of 3 or 4 carbon atoms; R' is a monovalent radical selected from a group consisting essentially of hydrogen and —(CH$_2$)$_n$SO$_3$M; R" is a monovalent radical selected from a group consisting essentially of —(CH$_2$)$_n$SO$_3$M and

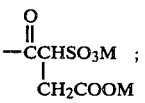

R''' is R' or R", M in all formulas is an alkali cation; n in all formulas has a value of 1, 2 or 3; x has a value of 0 or 1; and a has an average value of 0 to 3; and (C) a soluble silicate represented by the general formula

wherein M has the meaning set forth above and b has a value of 0.5 to 3.

Another aspect of this invention is an alcoholic composition comprising a combination of (A) an alcohol; (B) an alkali siliconate silylorganosulfonate which has the general formula

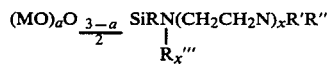

wherein R is a divalent alkylene radical of 3 or 4 carbon atoms; R' is a monovalent radical selected from a group consisting essentially of hydrogen and —(CH$_2$)$_n$SO$_3$M; R" is a monovalent radical selected from a group consisting essentially of —(CH$_2$)$_n$SO$_3$M and

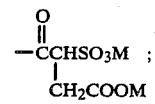

R''' is R' or R", M in all formulas is an alkali cation; n in all formulas has a value of 1, 2 or 3; x has a value of 0 or 1; and a has an average value of 0 to 3; and (C) a soluble silicate represented by the general formula

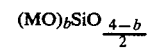

wherein M has the meaning set forth above and b has a value of 0.5 to 3.

Yet another aspect of this invention is a method of inhibiting metal corrosion in an aqueous medium by adding to the aqueous medium a composition comprising an alkali siliconate silylorganosulfonate which has the general formula

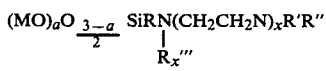

wherein R is a divalent alkylene radical of 3 or 4 carbon atoms; R' is a monovalent radical selected from a group consisting essentially of hydrogen and —(CH$_2$)$_n$SO$_3$M; R" is a monovalent radical selected from a group consisting essentially of —(CH$_2$)$_n$SO$_3$M and

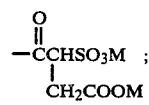

R''' is R' or R", M in all formulas is an alkali cation, n in all formulas has a value of 1, 2 or 3; x has a value of 0 or 1; and a has an average value of 0 to 3.

A further aspect of this invention is a method of inhibiting metal corrosion in an alcoholic medium by adding to the alcoholic medium a composition comprising an alkali siliconate silylorganosulfonate which has the general formula

wherein R is a divalent alkylene radical of 3 or 4 carbon atoms; R' is a monovalent radical selected from a group consisting essentially of hydrogen and —(CH$_2$)$_n$SO$_3$M;

R″ is a monovalent radical selected from a group consisting essentially of —(CH$_2$)$_n$SO$_3$M and

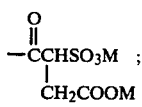

R‴ is R′ or R″, M in all formulas is an alkali cation; n in all formulas has a value of 1, 2 or 3; x has a value of 0 or 1; and a has an average value of 0 to 3.

Still another aspect of this invention is a method of inhibiting metal corrosion in an aqueous medium by adding to the aqueous medium a composition comprising (A) a siliconate which has the general formula

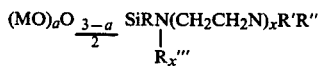

wherein R is a divalent alkylene radical of 3 or 4 carbon atoms; R′ is a monovalent radical selected from a group consisting essentially of hydrogen and —(CH$_2$)$_n$SO$_3$M; R″ is a monovalent radical selected from a group consisting essentially of —(CH$_2$)$_n$SO$_3$M and

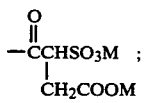

R‴ is R′ or R″, M in all formulas is an alkali cation; n in all formulas has a value of 1, 2 or 3; x has a value of 0 or 1; and a has an average value of 0 to 3; and (B) a soluble silicate represented by the general formula

wherein M has the meaning set forth above and b has a value of 0.5 to 3.

And yet another aspect of this invention is a method of inhibiting metal corrosion in an alcoholic medium by adding to the alcoholic medium a composition comprising (A) a siliconate which has the general formula

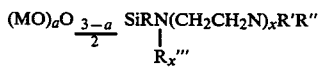

wherein R is a divalent alkylene radical of 3 or 4 carbon atoms; R′ is a monovalent radical selected from a group consisting essentially of hydrogen and —(CH$_2$)$_n$SO$_3$M; R″ is a monovalent radical selected from a group consisting essentially of —(CH$_2$)$_n$SO$_3$M and

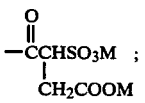

R‴ is R′ or R″, M in all formulas is an alkali cation; n in all formulas has a value of 1, 2 or 3; x has a value of 0 or 1; and a has an average value of 0 to 3; and, (B) a soluble silicate represented by the general formula

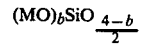

wherein M has the meaning set forth above and b has a value of 0.5 to 3.

Some silylorganosulfonates are known materials and some of them are commercially available. Silylorganosulfonates can be prepared by a number of methods which include, among others, the chlorosulfonic acid sulfonation of aralkylsilanes; the sulfonation of haloalkylarylsilanes using Na$_2$SO$_3$; the reaction of sodium sulfite with various organofunctional silanes such as

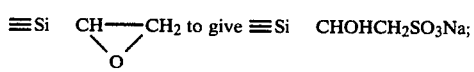

a two step reaction involving the reaction of aminosilanes with unsaturated anhydrides and the subsequent sulfonation of that reaction product by Na$_2$SO$_3$; the addition of active hydrogen functional silanes to propane sulfone; the oxidation of mercaptosilanes to the sulfonates; the reaction of formaldehyde-sodiumbisulfite adduct, HOCH$_2$SO$_3$Na, with aminofunctional organosilanes; and the addition of aminofunctional organosilanes to CH$_2$=CHSO$_3$Na. Details of the various methods used to prepare the sulfonates of this invention are set forth in the examples.

The simple silylalkyl or silylaryl sulfonates have a limited value as silicate stabilizers, and, therefore, there are certain limitations placed on the sulfonates useful in this invention. For example, simply silylmethyl sulfonates readily decompose in alkali at room temperature by cleavage of the silicon-carbon bond. Similarly, silylethyl sulfonate decomposes, but at a much slower rate. Silylpropyl sulfonates also decompose at room temperature under the influence of alkali, so that their usefulness is limited. Simple arylsilanes cannot be sulfonated as any attempts at sulfonation have resulted in cleavage of the aryl group from silicon.

The alkali siliconate silylorganosulfonates of this invention have the general formula,

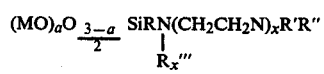

As can be observed from the above disclosure, the key to the inventive concepts herein is the use of certain, specifically defined, siliconate salts shown by the above formula.

For purposes of this invention, M can be selected from the alkali cationic groups which are the alkali metal cations and the tetraorganoammonium cations. Thus, M for purposes of this invention can be selected from sodium, potassium, lithium, rubidium and the tetraorganoammonium cations such as tetra(alkyl)ammonium cations; tetra- (mixed aryl-alkyl and mixed aralkyl-alkyl ammonium cations and the tetra(hydroxyalkyl)ammonium cations. Preferred are tetra(methyl)ammonium, tetra(ethyl)ammonium, phenyltrimethyl ammonium, benzyltrimethyl ammonium and tetra(hydroxyethy)ammonium cations. Also considered within the scope of this invention are the polyvalent cations produced by converting polyamines such as guanidine or ethylenediamine to poly ammonium hydroxides (See. U.S. Pat. No. 3,341,469, supra).

The unoccupied valences of the oxygen atoms attached to the silicon atoms of the siliconate salts can be occupied by M, hydrogen or another silicon atom as long as sufficient oxygen valences are occupied by M or hydrogen to provide compositions that are soluble in aqueous or alcoholic mediums. Generally, a can have an average value from 0 to 3 in the compositions of this invention. However, because polymerization by silanol condensation at a neutral pH can cause a loss of stability in solutions and eventual gelling, it is preferred that a has an average value of 1 to 3 so that at least one oxygen valence is occupied by an alkali metal cation or a tetraorganoammonium cation to provide more soluble compositions that remain stable in solution and do not gel for long periods of time. It should be understood however that an important aspect of the present invention is that the sulfonate functional organosiliconates of the instant invention remain dissolved and do not precipitate or form gels in aqueous or alcoholic mediums under a broader range of conditions of concentration and pH than the non-functional organosiliconates. Similarly, it should be understood that combinations of sulfonate functional organosiliconates of this invention and soluble silicates likewise remain dissolved and do not precipitate or form gels in aqueous or alcoholic mediums under a broader range of conditions of concentration and pH than the soluble silicates alone.

The siliconate salts of this invention can be prepared prior to their use in the inventive compositions herein or the siliconate salts can be prepared insitu. That is, certain of the siliconate salts herein can be prepared insitu by converting the acid forms of the siliconates to salts.

In the siliconate formula,

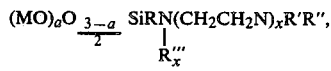

R represents a bridge between silicon and a nitrogen atom that is a divalent alkylene radical of 3 or 4 carbon atoms. R can be, for example, trimethylene, tetramethylene, 1-methyltrimethylene and 2-methyltrimethylene. Generally it is preferred that R is trimethylene because of the ready availability of these precursor aminofunctional organosilanes from which the sulfonates of this invention are most easily prepared.

R' in the formula is a monovalent radical attached to a nitrogen atom and is selected from a group consisting essentially of hydrogen and —(CH$_2$)$_n$SO$_3$M. Since n has a value of 1, 2 or 3, R' can be hydrogen, —CH$_2$SO$_3$M, —CH$_2$CH$_2$SO$_3$M, or —CH$_2$CH$_2$CH$_2$SO$_3$M.

R" in the formula is also a monovalent radical attached to a nitrogen atom. R" is selected from a group consisting essentially of —(CH$_2$)$_n$SO$_3$M and

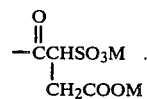

In all the formulas, n has a value of 1, 2 or 3, so that R" can be —CH$_2$SO$_3$M, —CH$_2$CH$_2$SO$_3$M, —CH$_2$CH$_2$CH$_2$SO$_3$M or

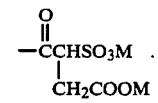

R'" in the formula is also a monovalent radical attached to a nitrogen atom. R'" can be either R' or R" so that R'" is selected from the group consisting essentially of hydrogen, —CH$_2$SO$_3$M, —CH$_2$CH$_2$SO$_3$M, —CH$_2$CH$_2$CH$_2$SO$_3$M and

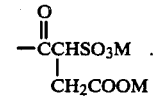

In all cases, M in the formulas for radicals R', R" or R'" is the same as previously described.

The siliconates that are operable in the present invention can contain one nitrogen atom or two nitrogen atoms in the bridge between the silicon atoms and the sulfonate groups. In the general formula x can be 0, in which case there is only one nitrogen atom in the bridging group. Also, x can be 1, in which case there are two nitrogens in the bridging group.

As mentioned earlier, the above described siliconates have many uses. The siliconates can be used alone or in conjunction with a silicate as will be explained below.

The siliconates themselves are corrosion inhibitors for metals, and thus they can be used in systems which require corrosion inhibitors. Thus, for example, the siliconates can be used in hydraulic systems, especially those hydraulic systems where polyglycols are used as hydraulic fluids.

These materials can also be used as corrosion inhibitors in heat transfer systems such as in automobile cooling systems, static pump cooling systems, boiler water systems and geothermal steam recovery and transfer systems. These materials can also be used in refrigeration units, air-conditioning units, cooling coils and other heat exchangers. Further, the siliconates can be used to stabilize soluble silicates. Thus, these siliconates can be used to stabilize silicates that are intentionally added to systems, such as, for example, the soluble silicates in antifreeze formulations and coolants. These siliconates can also be used in those systems where silicates naturally occur and where those naturally occurring silicates cause problems, such as, for example, in boiler water and geothermal steam systems.

The soluble silicates useful in this invention have the formula

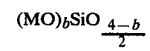

and are represented by such materials as alkali metal orthosilicates, alkali metal metasilicates, alkali metal tetrasilicates, the alkali metal disilicates and the tetraorganoammonium silicates. Whenever soluble silicates are referred to in this invention, it is intended that the inventor is referring to those known silicates which are soluble in water. The alkali cation represented by M can be any of the alkali metal cations such as sodium, potassium, lithium and rubidium or a tetraorganoammonium cation. The tetraorganoammonium cations can be selected from tetra(alkyl)ammonium cations; tetra- (mixed aryl-alkyl and mixed aralkyl-alkyl ammonium cations and the tetra(hydroxyalkyl)ammonium cations. Preferred are tetra(methyl)ammonium, tetra(ethyl)ammonium, phenyltrimethyl ammonium, benzyltrimethyl ammonium and tetra(hydroxyethyl)ammonium cations. Also considered within the scope of this invention are the polyvalent cations produced by converting polyamines such as guanidine or ethylenediamine to polyammonium hydroxides (See U.S. Pat. No. 3,341,469, supra).

The inventive method herein for stabilizing soluble silicates requires that certain defined siliconate salts be used in aqueous, alcoholic or aqueous-alcoholic systems that already contain soluble silicates, but it is also contemplated within the scope of this invention to form a composition from a siliconate salt of this invention and a soluble silicate and use this combination to treat aqueous, alcoholic or aqueous-alcoholic systems.

Thus, what is contemplated in this invention is the use of the above defined siliconate salts or combination of such siliconate salts and soluble silicates to treat aqueous, alcoholic or aqueous-alcoholic systems to enhance the stabilization of soluble silicates and to prevent corrosion of metals.

Such uses therefore include antifreezes, coolants and concentrates for use in automotive engine cooling systems, controlling scale in geothermal power plants, controlling scale in conventional heat exchange systems and the like. Also contemplated within the scope of this invention is the use of the siliconates in industrial and household cleaning compositions.

The amount of siliconate salt required to carry out the inventive method herein is dependent on the system in which the siliconate salt is used. Ordinarily, the siliconate salts are most useful at a few parts per million concentration to a few weight percent concentration. The siliconate salts can be used alone or in combination with soluble silicates. Generally combinations of 0.1 to 99.9 parts by weight of siliconate salt with 0.1 to 99.9 parts by weight of soluble silicate are useful in the invention.

When the system requires the addition of the siliconate salts to the soluble silicates before use, it is preferred that the two components are mixed in a ratio of about 0.1 to 20 mole percent of siliconate salt based on the silicate. Quantities less than 0.1 mole percent have been found to give less than optimum results while quantities greater than about 20 mole percent have been found to be wasteful. For automotive antifreeze applications, it is best to use about 1 part by weight of the siliconate-silicate mixture, based on 100 parts by weight of the aqueous alcohol system, to prevent corrosion.

The preferred amount of siliconate salt that is used when it is not required to premix the siliconate salt with the silicate is about 50 ppm to 5 weight percent based on the weight of the total system it is being used in. For example, if the siliconate salt is used to stabilize soluble silicates in geothermal steam, one only needs to ascertain the amount of soluble silicate that is present in such steam and add an amount of siliconate salt equivalent to 0.1 to 20 mole percent of the siliconate salt based on the silicate present in the steam water. In other water systems, larger quantities may be required. The preferred range of use of the siliconates for all systems within the scope of this invention is about 100 parts by weight per million parts by weight of the total system to 5 parts by weight of the siliconate per 100 parts by weight of the total system.

When the siliconate salt is used with the soluble silicate, there must be some water present in the system. Relatively large amounts of water can be used in alcoholic systems or, small amounts, i.e. 80–98 weight percent, of alcohol can be used in the alcohol systems. Thus, the aqueous alcoholic compositions may be "concentrates", coolants, or antifreeze compositions.

The alcohols that are useful in this invention include both monomeric alcohols such as methanol, ethanol, propanol and butanol and polyhydric alcohols such as ethylene glycol, diethylene glycol, triethylene glycol, propylene glycol, glycerol, mixtures of the above and mixtures of the above alcohols with their ethers.

The siliconate salt-soluble silicate combination can be easily prepared by simply mixing the siliconate salt with the soluble silicate. It should be noted that the siliconate salt, when used to stabilize systems already containing the soluble silicate, is simply added to such systems and stirred to homogenize.

The siliconate salt-soluble silicate combination can also be formed in-situ, that is the sulfonic acid functional silane precursor of the siliconate salt can be added to an aqueous, alcoholic or aqueous-alcoholic system and the system can be treated with, for example, NaOH to yield the siliconate salt. Sometimes, there may be enough cationic material already in such a system to accomplish the salt formation.

It is within the scope of this invention to add various additives which impart special properties such as antifoam agents, both organic and siloxane based dyes, pH indicators, other inhibitors such as corrosion inhibitors, thickeners and the like.

Now, so that those skilled in the art understand and appreciate the invention, the following examples are offered. These examples should not be construed as limiting that which is set out and claimed as the invention in the appended claims.

EXAMPLE 1

Preparation of

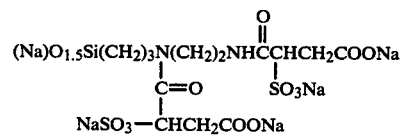

Twenty-two gms of $(CH_3O)_3Si(CH_2)_3NH(CH_2)_2NH_2$ were placed in a round-bottomed, three-necked glass reaction vessel which was equipped with a stirrer and a thermometer and a solids addition apparatus. To the silane was added 100 ml of isopropanol and with stirring, twenty gms of maleic anhydride (0.2 mol) was also added. An exothermic reaction ensued and resulted in a clear solution after a short time. This material was identified as

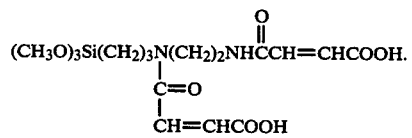

This product was diluted with 100 ml of distilled water and neutralized with 16 gms of 50 weight percent aqueous NaOH (0.2 mol). This neutral solution was stirred with 26 gms of $Na_2SO_3$ (0.2 mol) while the mixture was warmed enough to distill off the isopropanol solvent and the by-produced methanol. The product was then diluted to 200 gms total using distilled water to give a strong alkaline solution of 1 molal bis-sulfosuccinate amide of the diaminosilane.

EXAMPLE 2

Twenty-two gms of $(CH_3CH_2O)_3Si(CH_2)_3NH_2$ was added to a mixture of 21 gms of $NaHSO_3$, 16.2 gms of 37% aqueous formaldehyde and 50 gms of water. The mixture of reactants exothermed to 65° C. After cooling, the product was a clear aqueous solution of $O_{3/2}Si(CH_2)_3N(CH_2SO_3Na)_2$.

EXAMPLE 3

In a manner similar to example 1, two hundred twenty-one gms of $(CH_3CH_2O)_3Si(CH_2)_3NH_2$; 200 gms of isopropanol and 100 gms of maleic anhydride were combined to give $$(CH_3CH_2O)_3Si(CH_2)_3NH\overset{O}{\overset{\|}{C}}CH=CHCOOH.$$

To this compound there was added 126 gms of $Na_2SO_3$ in 600 gms of water containing 4 gms of NaOH pellets. An exothermic reaction ensued. The mixture was stirred while volatile materials were removed by heating to a temperature of 100° C. The result was about 1000 gms of a 1 molal solution $$(Na)O_{1.5}Si(CH_2)_3NH\overset{O}{\overset{\|}{C}}\underset{\underset{SO_3Na}{|}}{C}HCH_2COONa.$$

EXAMPLE 4

Preparation of Sulfonitropropylamines

Twenty-two gms of $(CH_3O)_3Si(CH_2)_3NH(CH_2)_2NH_2$, 46 gms of isopropanol and 24 gms of propane sultone (0.2 mols) were combined and the reaction exothermed to 70° C. The reaction was heated to 70° C. for 2 hours to give a neutral solution which contained the zwitterion $$O_{1.5}Si(CH_2)_3\underset{\underset{CH_2CH_2CH_2SO_3H}{|}}{N}CH_2CH_2NHCH_2CH_2CH_2SO_3H \rightleftarrows O_{1.5}Si(CH_2)_3\underset{\underset{CH_2CH_2CH_2SO_3^{\ominus}}{|}}{\overset{\oplus}{N}}HCH_2CH_2\overset{\oplus}{N}HCH_2CH_2CH_2SO_3^{\ominus}$$

Treatment with sodium hydroxide gave the sodium salt.

EXAMPLE 5

Derivatives of $(MeO)_3Si(CH_2)_3NHCH_2CH_2NH_2$ containing 1, 2 and 3 methylsulfonate groups were prepared by the method of example 2.

(A) Twenty-two gms of the silane was added to 10.5 gms of $NaHSO_3$, 8.1 gms of 37% aqueous formaldehyde and 60 gms of water. The product was an aqueous solution of predominately monosubstituted aminomethylsulfonate.

(B) Twenty-two gms of the silane was added to 21 gms of $NaHSO_3$, 16.2 gms of 37% aqueous formaldehyde and 60 gms of water. The product was an aqueous solution of predominately disubstituted aminomethylsulfonate represented by the formula $$O_{3/2}Si(CH_2)_3\underset{\underset{CH_2SO_3Na}{|}}{N}CH_2CH_2NHCH_2SO_3Na.$$

(C) Eleven gms of the silane was added to 15.8 gms of $NaHSO_3$, 12.5 gms of 37% aqueous formaldehyde and 60 gms of water. The product was an aqueous solution of trisubstituted aminomethylsulfonate of the formula $$O_{3/2}Si(CH_2)_3\underset{\underset{CH_2SO_3Na}{|}}{N}CH_2CH_2N(CH_2SO_3Na)_2.$$

EXAMPLE 6

Some of the siliconates of this invention were mixed with aqueous sodium silicate (3.22:1 ratio of $SiO_2:Na_2O$) as 1/6 molar solutions (1% $SiO_2$) in the ratios indicated in Table I. After equilibration for one hour at room temperature, the mixtures were neutralized to a pH of 7 to 8 with 10% aqueous hydrochloric acid. Dilute hydrochloric acid was added periodically to maintain a pH of 7 to 8. The neutralized solutions were observed periodically, and the point in time at which they gelled was considered to be the time of failure of the sulfonate to stabilize the silicate. The results are in Table I.

TABLE I

| | Stability of Sulfonate Siliconates at 25° C. in hours Molar Ratio of siliconate to silicate - 1: | | | | | | | |
|---|---|---|---|---|---|---|---|---|
| Functional Group on Silicon | 10 | 20 | 30 | 40 | 50 | 75 | 100 | ∞ |
| (1)[a] —$CH_2CH(CH_3)CH_2SO_3Na$ | * | 24 | 12 | — | — | — | — | 2 |
| (2)[a] —$(CH_2)_3OCH_2CH(OH)$—$CH_2SO_3Na$ | * | * | * | 168 | 72 | — | 24 | 2 |
| (3) —$(CH_2)_3NH(Q)$ | * | * | * | * | * | 24 | 8 | 2 |
| (4) —$(CH_2)_3N(Q)CH_2CH_2NHQ$ | * | * | 24 | 72 | 6 | 8 | 18 | 2.5 |
| (5) —$(CH_2)_3NCH_2CH_2NH(CH_2)_3SO_3Na$<br>   \|<br>   $(CH_2)_3SO_3Na$ | * | * | * | * | * | 6 | 7 | 2 |

\* = no gel in 7 days $Q = -\overset{O}{\overset{\|}{C}}-\underset{\underset{SO_3Na}{|}}{C}HCH_2COONa$

[a]shown for comparison purposes, not included in the present invention.

EXAMPLE 7

Stability in Hot Alkali

One molar alkali sulfonate siliconates were mixed in a 1:20 ratio with 1 molar sodium silicate (3.22 $SiO_2/Na_2O$ ratio) to give 6% $SiO_2$. Duplicate portions of the mixture were aged either at room temperature for 0.5 hours or at 90° C. for 2 hours. After the aging, the mixtures were neutralized to a phenolphthalein endpoint with 10 percent aqueous HCl, and the time from neutralization until gel formation was recorded for each solution. The time of gel formation is considered to be the time of failure of the sulfonate functional siliconate to stabilize the silicate. The results are shown in Table II where some phosphonate, carboxylate, and other sulfonate functional siliconates outside the scope of this invention are also included for comparison purposes.

from neutralization until gel formation was recorded for each solution. The time of gel formation is considered to be the time of failure of the sulfonate functional siliconate to stabilize the silicate. The ability of the siliconates to stabilize the silicate solutions is shown not to be impaired by the hot alkaline treatment. The results are shown in Table III.

TABLE II
Stability of Siliconates in Hot Alkali

| Functional group on Silicon | Gel Time After Neutralization In Seconds | |
|---|---|---|
| | 30 minutes aging at Room Temperature | 120 minutes aging at 90° C. |
| 1. $-(CH_2)_3OP(=O)(CH_3)-ONa$* | 22 | 24 |
| 2. $-CH_2CH_2COONa$* | 18 | 20 |
| 3. $-(CH_2)_3NCH_2CH_2N(CH_2CH_2COONa)_2$* with $CH_2CH_2COONa$ branch | 35 | 45 |
| 4. $-CH_2CH_2SCH_2COONa$* | 45 | 40 |
| 5. $-CH_2CH_2CH(CH_3)COONa$* | 40 | 45 |
| 6. $-(CH_2)_3OCH_2CH(OH)-CH_2SO_3Na$* | 35 | 40 |
| 7. $-CH_2CH_2CH_2SO_3K$* | 10 | 5 |
| 8. $-(CH_2)_3NH-C(=O)-CH(SO_3Na)-CH_2COONa$ | 90 | 60 |
| 9. $-(CH_2)_3N(O=C-CH(SO_3Na)-CH_2COONa)-CH_2CH_2NHC(=O)-CH(SO_3Na)CH_2COONa$ | 75 | 45 |
| 10. $-(CH_2)_3NCH_2CH_2NH(CH_2)_3SO_3Na$ with $(CH_2)_3SO_3Na$ branch | 100 | 200 |
| 11. -Control (no siliconate) | 4 | 5 |

*Shown for comparison purposes only, not included in the present invention.

TABLE III
Stability of Siliconates in Hot Alkali

| Functional group on Silicon | Gel Time After Neutralization In Seconds 1 day aging at Room Temperature/2 hours aging at 90° C. |
|---|---|
| 1. $-(CH_2)_3NHCH_2SO_3Na$ | 12   32 |
| 2. $-(CH_2)_3N(CH_2SO_3Na)_2$ | 29   33 |
| 3. $-(CH_2)_3NHCH_2CH_2NHCH_2SO_3Na$ | 6    8 |
| 4. $-(CH_2)_3NCH_2CH_2NHCH_2SO_3Na$ with $CH_2SO_3Na$ branch | 13   16 |
| 5. $-(CH_2)_3NCH_2CH_2N(CH_2SO_3Na)_2$ with $CH_2SO_3Na$ branch | 95   220 |

EXAMPLE 8

The sulfonates from example 2 and example 5 were evaluated as silicate stabilizers both with and without prior aging in hot alkaline solutions. One molar solutions of the sulfonates were mixed in a 1:20 ratio with 1 molar sodium silicate (3.22 $SiO_2/Na_2O$ ratio) to give 6% $SiO_2$. Duplicate portions were aged either at room temperature for 1 day or at 90° C. for 2 hours. After the aging, the mixtures were neutralized to a phenolphthalein endpoint with 10 percent aqueous HCl, and the time That which is claimed is:

1. A composition of matter which is an alkali siliconate silylorganosulfonate which has the general formula

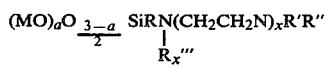

wherein
R is a divalent alkylene radical of 3 or 4 carbon atoms;
R' is a monovalent radical selected from a group consisting essentially of hydrogen and —(CH$_2$)$_n$SO$_3$M;
R" is a monovalent radical selected from a group consisting essentially of —(CH$_2$)$_n$SO$_3$M and

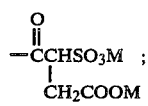

R'" is R' or R";
M in all formulas is an alkali cation;
n is all formulas has a value of 1, 2 or 3;
x has a value of 0 or 1; and
a has an average value of 0 to 3.

2. The composition of claim 1 wherein M is an alkali metal cation and x is 0.

3. The composition of claim 2 wherein M is sodium, R' is hydrogen and R" is

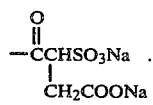

4. The composition of claim 2 wherein M is sodium, R' is hydrogen and R" is —CH$_2$SO$_3$Na.

5. The composition of claim 2 wherein M is sodium, R' is —CH$_2$SO$_3$Na and R" is —CH$_2$SO$_3$Na.

6. The composition of claim 1 wherein M is an alkali metal cation and x is 1.

7. The composition of claim 6 wherein M is sodium, R' is hydrogen, R" is

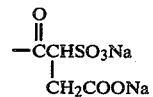

and R'" is

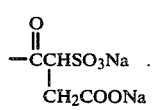

8. The composition of claim 6 wherein M is sodium, R" is —(CH$_2$)$_n$SO$_3$Na and R'" is —(CH$_2$)$_n$SO$_3$Na.

9. The composition of claim 8 wherein R' is —CH$_2$SO$_3$Na and n is 1.

10. The composition of claim 8 wherein R' is hydrogen and n is 3.

11. A composition of matter which is comprised of (A) 0.1 to 99.9 parts by weight of an alkali siliconate silylorganosulfonate which has the general formula

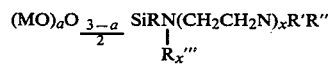

wherein
R is a divalent alkylene radical of 3 or 4 carbon atoms;
R' is a monovalent radical selected from a group consisting essentially of hydrogen and —(CH$_2$)$_n$SO$_3$M;
R" is a monovalent radical selected from a group consisting essentially of —(CH$_2$)$_n$SO$_3$M and

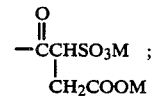

R'" is R' or R";
M in all formulas is an alkali cation;
n in all formulas has a value of 1, 2 or 3;
x has a value of 0 or 1; and
a has an average value of 0 to 3; and (B) 0.1 to 99.9 parts by weight of a soluble silicate represented by the general formula

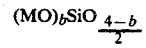

wherein M has the meaning set forth above and b has an average value of 0.5 to 3.

12. The composition of claim 11 wherein M is an alkali metal cation and x is 0.

13. The composition of claim 12 wherein M is sodium, R' is hydrogen and R" is

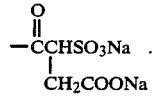

14. The composition of claim 12 wherein M is sodium, R' is hydrogen and R" is —CH$_2$SO$_3$Na.

15. The composition of claim 12 wherein M is sodium, R' is —CH$_2$SO$_3$Na and R" is —CH$_2$SO$_3$Na.

16. The composition of claim 11 wherein M is an alkali metal cation and x is 1.

17. The composition of claim 16 wherein M is sodium, R' is hydrogen, R" is

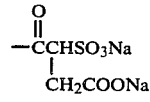

and R'" is

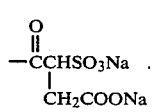

18. The composition of claim 16 wherein M is sodium, R" is —(CH$_2$)$_n$SO$_3$Na and R'" is —(CH$_2$)$_n$SO$_3$Na.

19. The composition of claim 18 wherein R' is —CH$_2$SO$_3$Na and n is 1.

20. The composition of claim 18 wherein R' is hydrogen and n is 3.

21. An aqueous composition comprising a combination of (A) water; (B) an alkali siliconate silylorganosulfonate which has the general formula

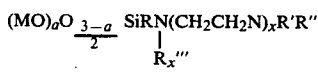

wherein

R is a divalent alkylene radical of 3 or 4 carbon atoms;

R' is a monovalent radical selected from a group consisting essentially of hydrogen and —(CH$_2$)$_n$SO$_3$M;

R" is a monovalent radical selected from a group consisting essentially of —(CH$_2$)$_n$SO$_3$M and

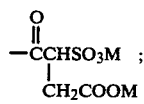

R'" is R' or R";

M in all formulas is an alkali cation;

n in all formulas has a value of 1, 2 or 3;

x has a value of 0 or 1; and a has an average value of 0 to 3; and (C) a soluble silicate represented by the general formula

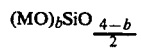

wherein M has the meaning set forth above and b has an average value of 0.5 to 3.

22. The composition of claim 21 wherein M is an alkali metal cation and x is 0.

23. The composition of claim 22 wherein M is sodium, R' is hydrogen and R" is

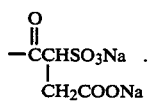

24. The composition of claim 22 wherein M is sodium, R' is hydrogen and R" is —CH$_2$SO$_3$Na.

25. The composition of claim 22 wherein M is sodium, R' is —CH$_2$SO$_3$Na and R" is —CH$_2$SO$_3$Na.

26. The composition of claim 21 wherein M is an alkali metal cation and x is 1.

27. The composition of claim 26 wherein M is sodium, R' is hydrogen, R" is

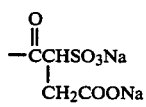

and R'" is

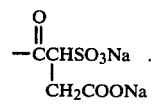

28. The composition of claim 26 wherein M is sodium, R" is —(CH$_2$)$_n$SO$_3$Na and R'" is —(CH$_2$)$_n$SO$_3$Na.

29. The composition of claim 28 wherein R' is —CH$_2$SO$_3$Na and n is 1.

30. The composition of claim 28 wherein R' is hydrogen and n is 3.

31. An alcoholic composition comprising a combination of (A) an alcohol;

(B) an alkali siliconate silylorganosulfonate which has the general formula

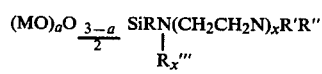

wherein

R is a divalent alkylene radical of 3 or 4 carbon atoms;

R' is a monovalent radical selected from a group consisting essentially of hydrogen and —(CH$_2$)$_n$SO$_3$M;

R" is a monovalent radical selected from a group consisting essentially of —(CH$_2$)$_n$SO$_3$M and

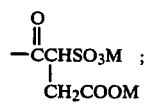

R'" is R' or R";

M in all formulas is an alkali cation;

n in all formulas has a value of 1, 2 or 3;

x has a value of 0 or 1; and a has an average value of 0 to 3; and (C) a soluble silicate represented by the general formula

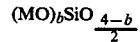

wherein M has the meaning set forth above and b has an average value of 0.5 to 3.

32. The composition of claim 31 wherein M is an alkali metal cation and x is 0.

33. The composition of claim 32 wherein M is sodium, R' is hydrogen and R" is

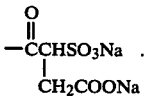

34. The composition of claim 32 wherein M is sodium, R' is hydrogen and R" is —CH$_2$SO$_3$Na.

35. The composition of claim 32 wherein M is sodium, R' is —CH$_2$SO$_3$Na and R" is —CH$_2$SO$_3$Na.

36. The composition of claim 31 wherein M is an alkali metal cation and x is 1.

37. The composition of claim 36 wherein M is sodium, R' is hydrogen, R" is

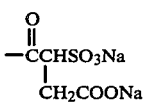

and R''' is

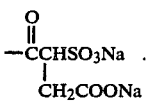

38. The composition of claim 36 wherein M is sodium, R" is —(CH$_2$)$_n$SO$_3$Na and R''' is —(CH$_2$)$_n$SO$_3$Na.

39. The composition of claim 38 wherein R' is —CH$_2$SO$_3$Na and n is 1.

40. The composition of claim 39 wherein R' is hydrogen and n is 3.

41. A method of inhibiting corrosion of metal in contact with an aqueous medium, the method comprising adding to the aqueous medium or forming in-situ a corrosion inhibiting amount of a composition consisting of an alkali siliconate silylorganosulfonate which has the general formula

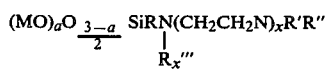

wherein
R is a divalent alkylene radical of 3 or 4 carbon atoms;
R' is a monovalent radical selected from a group consisting essentially of hydrogen and —(CH$_2$)$_n$SO$_3$M;
R" is a monovalent radical selected from a group consisting essentially of —(CH$_2$)$_n$SO$_3$M and

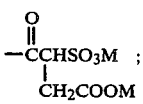

R''' is R' or R";
M in all formulas is an alkali cation;
n in all formulas has a value of 1, 2 or 3;
x has a value of 0 or 1; and
a has an average value of 0 to 3.

42. The method of claim 41 wherein M is an alkali metal cation and x is 0.

43. The method of claim 42 wherein M is sodium, R' is hydrogen and R" is

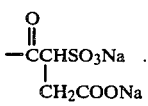

44. The method of claim 42 wherein M is sodium, R' is hydrogen and R" is —CH$_2$SO$_3$Na.

45. The method of claim 42 wherein M is sodium, R' is —CH$_2$SO$_3$Na and R" is —CH$_2$SO$_3$Na.

46. The method of claim 41 wherein M is an alkali metal cation and x is 1.

47. The method of claim 46 wherein M is sodium, R' is hydrogen, R" is

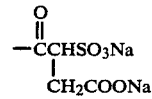

and R''' is

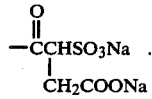

48. The method of claim 46 wherein M is sodium, R" is —(CH$_2$)$_n$SO$_3$Na and R''' is —(CH$_2$)$_n$SO$_3$Na.

49. The method of claim 48 wherein R' is —CH$_2$SO$_3$Na and n is 1.

50. The method of claim 48 wherein R' is hydrogen and n is 3.

51. A method of inhibiting corrosion of metal in contact with an alcoholic medium, the method comprising adding to the alcoholic medium or forming in-situ a corrosion inhibiting amount of a composition consisting of an alkali siliconate silylorganosulfonate which has the general formula

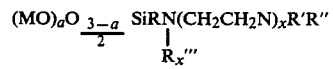

wherein
R is a divalent alkylene radical of 3 or 4 carbon atoms;
R' is a monovalent radical selected from a group consisting essentially of hydrogen and —(CH$_2$)$_n$SO$_3$M;
R" is a monovalent radical selected from a group consisting essentially of —(CH$_2$)$_n$SO$_3$M and

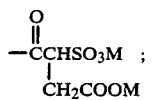

R''' is R' or R";
M in all formulas is an alkali cation;
n in all formulas has a value of 1, 2 or 3;
x has a value of 0 or 1; and
a has an average value of 0 to 3.

52. The method of claim 51 wherein M is an alkali metal cation and x is 0.

53. The method of claim 52 wherein M is sodium, R' is hydrogen and R" is

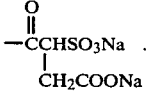

54. The method of claim 52 wherein M is sodium, R' is hydrogen and R" is —CH$_2$SO$_3$Na.

55. The method of claim 52 wherein M is sodium, R' is —CH$_2$SO$_3$Na and R" is —CH$_2$SO$_3$Na.

56. The method of claim 51 wherein M is an alkali metal cation and x is 1.

57. The method of claim 56 wherein M is sodium, R' is hydrogen, R" is

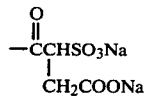

and R''' is

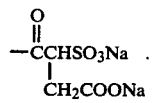

58. The method of claim 56 wherein M is sodium, R" is —(CH$_2$)$_n$SO$_3$Na and R''' is —(CH$_2$)$_n$SO$_3$Na.

59. The method of claim 58 wherein R' is —CH$_2$SO$_3$Na and n is 1.

60. The method of claim 58 wherein R' is hydrogen and n is 3.

61. A method of stabilizing soluble silicates comprising adding to the soluble silicates 0.001 to 100 parts by weight based on the weight of soluble silicates of a composition consisting of an alkali siliconate silylorganosulfonate which has the general formula

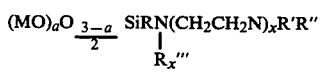

wherein

R is a divalent alkylene radical of 3 or 4 carbon atoms;

R' is a monovalent radical selected from a group consisting essentially of hydrogen and —(CH$_2$)$_n$SO$_3$M;

R" is a monovalent radical selected from a group consisting essentially of —(CH$_2$)$_n$SO$_3$M and

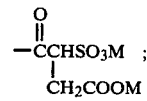

R''' is R' or R";

M in all formulas is an alkali cation;

n in all formulas has a value of 1, 2 or 3;

x has a value of 0 or 1; and a has an average value of 0 to 3.

62. The method of claim 61 wherein M is an alkali metal cation and x is 0.

63. The method of claim 62 wherein M is sodium, R' is hydrogen and R" is

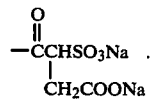

64. The method of claim 62 wherein M is sodium, R' is hydrogen and R" is —CH$_2$SO$_3$Na.

65. The method of claim 62 wherein M is sodium, R' is —CH$_2$SO$_3$Na and R" is —CH$_2$SO$_3$Na.

66. The method of claim 61 wherein M is an alkali metal cation and x is 1.

67. The method of claim 66 wherein M is sodium, R' is hydrogen, R" is

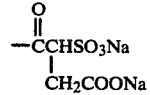

and R''' is

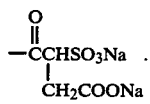

68. The method of claim 66 wherein M is sodium, R" is —(CH$_2$)$_n$SO$_3$Na and R''' is —(CH$_2$)$_n$SO$_3$Na.

69. The method of claim 68 wherein R' is —CH$_2$SO$_3$Na and n is 1.

70. The method of claim 68 wherein R' is hydrogen and n is 3.

* * * * *

UNITED STATES PATENT AND TRADEMARK OFFICE
CERTIFICATE OF CORRECTION

PATENT NO. : 4,503,242

DATED : March 5, 1985

INVENTOR(S) : Edwin P. Plueddemann

It is certified that error appears in the above-identified patent and that said Letters Patent is hereby corrected as shown below:

Col. 1, line 64, delete "gellation and substitute therefor -- gelation --.

Col. 6, line 15, delete "$\equiv$Si  $\underset{\underset{O}{\diagdown\diagup}}{CH-CH_2}$  to give $\equiv$Si  $CHOHCH_2SO_3Na;$"

and substitute therefor -- $\equiv$Si-$\underset{\underset{O}{\diagdown\diagup}}{CH-CH_2}$  to give $\equiv$Si-$CHOHCH_2SO_3Na;$ --.

Col. 6, line 33, delete "simply" and substitute therefor -- simple --.

Col. 6, lines 59-60, delete "tetra- (mixed aryl-alkyl and mixed aralkyl-alkyl ammonium" and substitute therefor -- tetra(mixed aryl-alkyl and mixed aralkyl-alkyl)ammonium --.

Col. 6, line 64, delte "droxyethy)ammonium" and substitute therefor -- droxyethyl)ammonium --.

Col. 8, line 68 to Col. 9, line 1, delete "tetra- (mixed aryl-alkyl and mixed aralkyl-alkyl ammonium" and substitute therefor -- tetra(mixed aryl-alkyl and mixed aralkyl-alkyl)-ammonium --.

Col. 11, line 49, delete "(0.2 mols) and substitute therefor -- (0.2 mol) --.

Col. 13, line 7, delete "hours" and substitute therefor -- hour --.

Table II, #11, delete "-Control (no siliconate)" and substitute therefor -- Control (no siliconate) --.

UNITED STATES PATENT AND TRADEMARK OFFICE
CERTIFICATE OF CORRECTION

PATENT NO. : 4,503,242

DATED : March 5, 1985

INVENTOR(S) : Edwin P. Plueddemann

It is certified that error appears in the above-identified patent and that said Letters Patent is hereby corrected as shown below:

Col. 15, line 26, delete "n is" and substitute therefor -- n in --.

Col. 19, line 22, delete "39" and substitute therefor -- 38 --.

Signed and Sealed this

Eleventh Day of February 1986

[SEAL]

Attest:

DONALD J. QUIGG

Attesting Officer

Commissioner of Patents and Trademarks